(12) United States Patent
Sakamoto et al.

(10) Patent No.: US 9,354,161 B2
(45) Date of Patent: May 31, 2016

(54) SAMPLE ANALYZING METHOD AND SAMPLE ANALYZER

(71) Applicant: Sysmex Corporation, Kobe-shi, Hyogo (JP)

(72) Inventors: Mitsumasa Sakamoto, Kobe (JP); Masatsugu Ozasa, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 14/470,521

(22) Filed: Aug. 27, 2014

(65) Prior Publication Data

US 2015/0064742 A1 Mar. 5, 2015

(30) Foreign Application Priority Data

Aug. 30, 2013 (JP) ................................ 2013-178939

(51) Int. Cl.
| | | |
|---|---|---|
| *G01N 21/00* | (2006.01) | |
| *G01N 21/21* | (2006.01) | |
| *G01N 33/50* | (2006.01) | |
| *G01N 15/14* | (2006.01) | |
| *G01N 15/00* | (2006.01) | |
| *G01N 21/05* | (2006.01) | |

(52) U.S. Cl.
CPC .............. *G01N 21/21* (2013.01); *G01N 15/147* (2013.01); *G01N 15/1429* (2013.01); *G01N 15/1434* (2013.01); *G01N 33/5005* (2013.01); *G01N 21/05* (2013.01); *G01N 2015/0065* (2013.01); *G01N 2015/0073* (2013.01); *G01N 2015/1402* (2013.01); *G01N 2201/06113* (2013.01); *G01N 2201/125* (2013.01)

(58) Field of Classification Search
CPC .............. G01N 2015/1486; G01N 2015/0084; G01N 15/1484; G01N 2015/0073; G01N 2500/04; G01N 2500/10; G01N 11/04; G01N 15/147; G01N 2015/008; G01N 2015/1413; G01N 21/1702; G01N 33/5029; G01N 33/54313
See application file for complete search history.

(56) References Cited

U.S. PATENT DOCUMENTS

| | | | |
|---|---|---|---|
| 5,017,497 A | * | 5/1991 | Gerard de Grooth ............... G01N 15/1434 250/461.2 |
| 6,118,522 A | | 9/2000 | Kanai et al. |
| 7,674,622 B2 | | 3/2010 | Garrett et al. |

(Continued)

FOREIGN PATENT DOCUMENTS

JP 11-23446 A 1/1999

OTHER PUBLICATIONS

Frita, R. et al., "Simple Flow Cytometric Detection of Haemozoin Containing Leukocytes and Erythrocytes for Research on Diagnosis, Immunology and Drug Sensitivity Testing", *Malaria Journal*, vol. 10, No. 1, Mar. 31, 2011, pp. 1-14.

(Continued)

*Primary Examiner* — Michael P Stafira
(74) *Attorney, Agent, or Firm* — Brinks Gilson & Lione

(57) ABSTRACT

Disclosed is a sample analyzing method comprising: flowing a measurement specimen prepared by mixing a sample and reagent through a flow cell; irradiating particles in the measurement specimen flowing through the flow cell with linearly polarized light and thereby producing scattered light; detecting a change of polarization condition of the scattered light produced by the particles; and discriminating erythrocytes from crystals in the measurement specimen based on the change of polarization condition.

21 Claims, 11 Drawing Sheets

(56) References Cited

U.S. PATENT DOCUMENTS

| | | |
|---|---|---|
| 8,148,101 B2 | 4/2012 | Kim et al. |
| 8,501,482 B2 | 8/2013 | Tanaka et al. |
| 2003/0030783 A1* | 2/2003 | Roche et al. .................... 356/39 |
| 2008/0014574 A1* | 1/2008 | Viator et al. ..................... 435/4 |
| 2009/0170149 A1* | 7/2009 | Viator et al. .................... 435/29 |
| 2010/0021878 A1* | 1/2010 | Kim et al. ....................... 435/2 |
| 2011/0045525 A1 | 2/2011 | Krockenberger et al. |
| 2011/0178716 A1* | 7/2011 | Krockenberger et al. ...... 702/19 |
| 2013/0078668 A1 | 3/2013 | Levine et al. |
| 2013/0314526 A1* | 11/2013 | Yasuda et al. .................. 348/79 |

OTHER PUBLICATIONS

Rebelo, M. et al., "A Novel Flow Cytometric Hemozoin Detection Assay for Real-Time Sensitivity Testing of Plasmodioum Falciparum", *PLOS ONE*, vol. 8, No. 4, Apr. 2013, pp. 1-12.

* cited by examiner

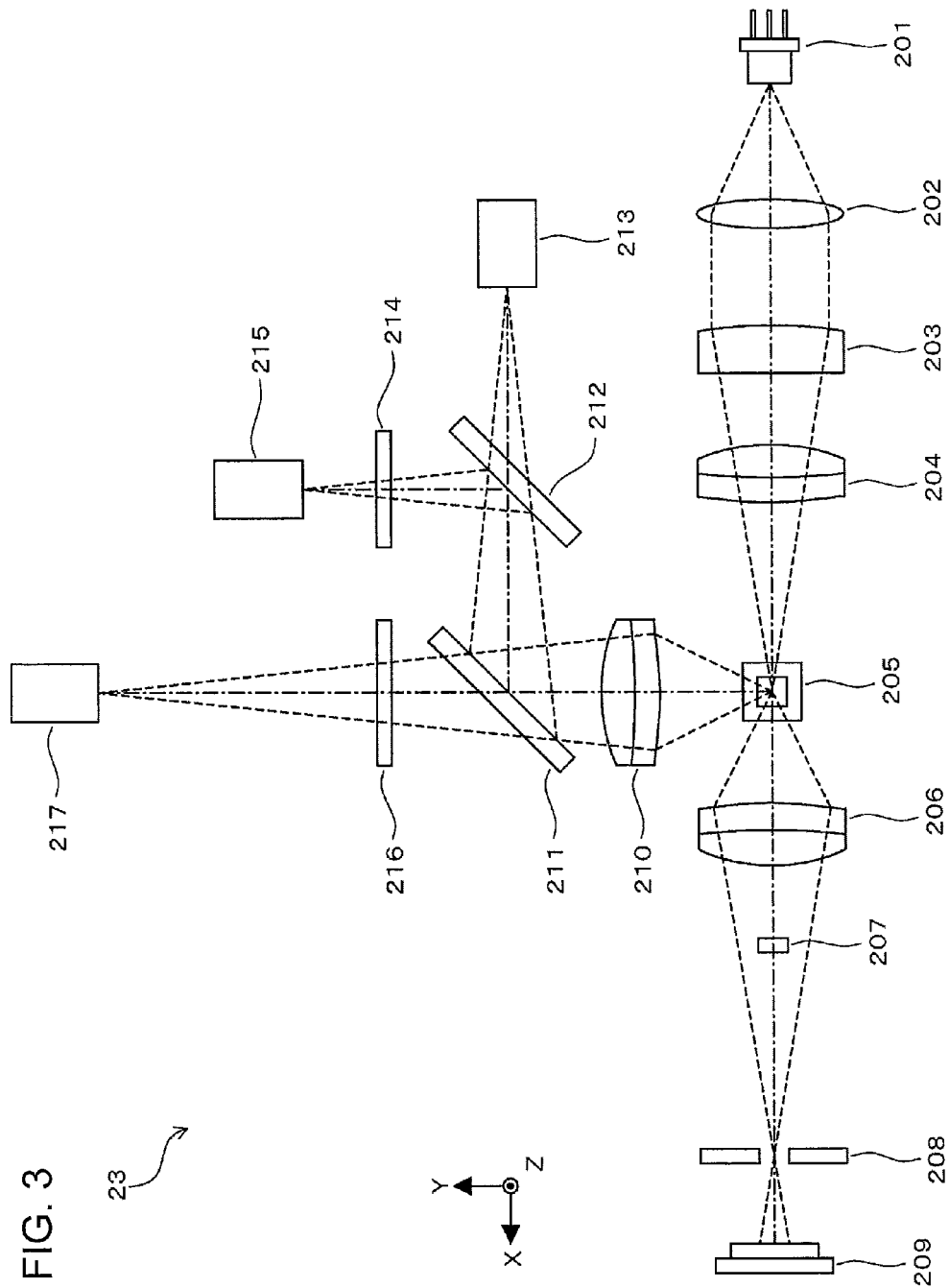

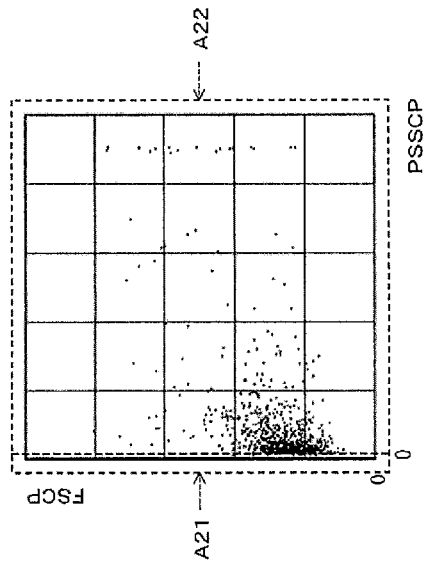
FIG. 7A FIRST SCATTERGRAM
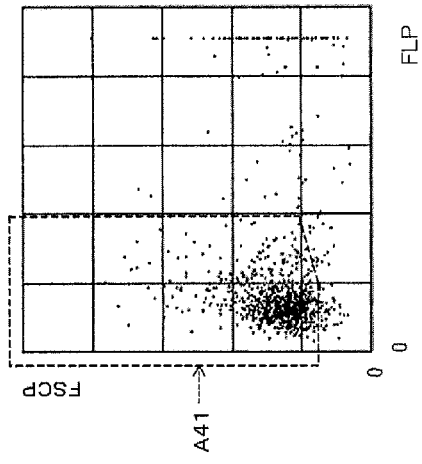
FIG. 7B SECOND SCATTERGRAM
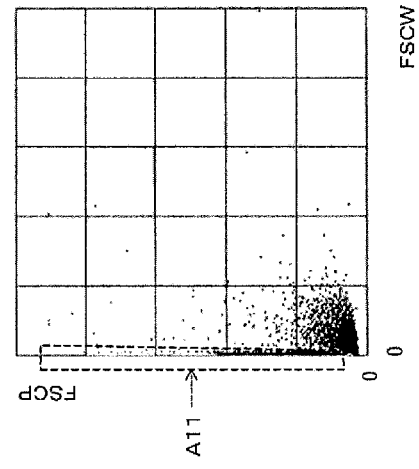
FIG. 7C THIRD SCATTERGRAM
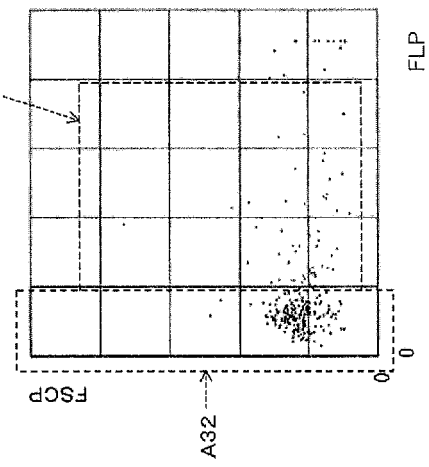
FIG. 7D FOURTH SCATTERGRAM FIG. 8A
| | Visual | Embodiment |
|---|---|---|
| Erythrocytes | 2288.0 / μL | 2315.3 / μL |
| Crystals | 0.0 / μL | 1.4 / μL |
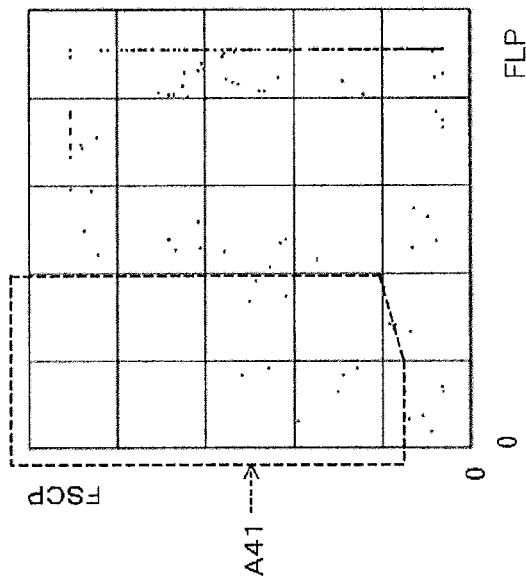
FIG. 8C
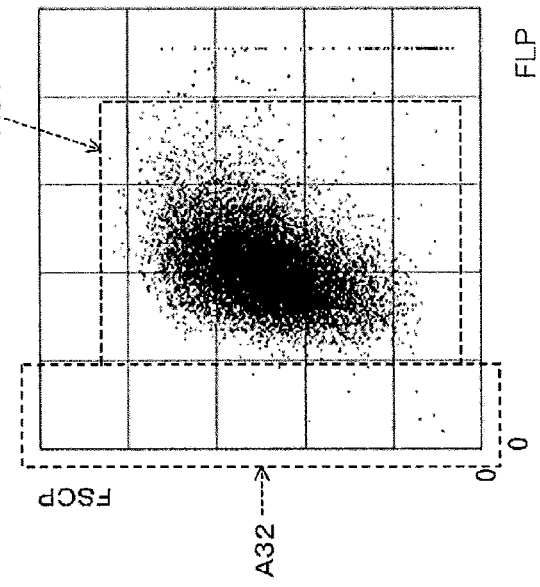
FIG. 8B FIG. 9A
FIG. 9B THIRD SCATTERGRAM
FIG. 9C FOURTH SCATTERGRAM
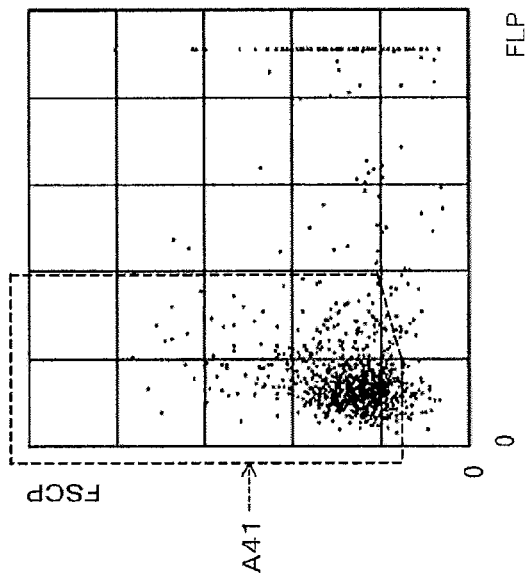
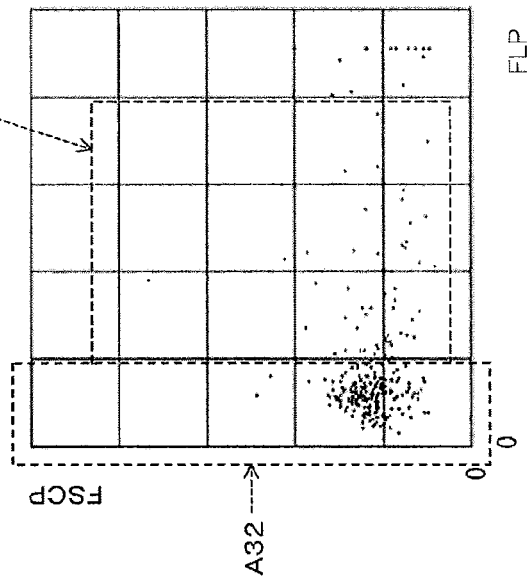

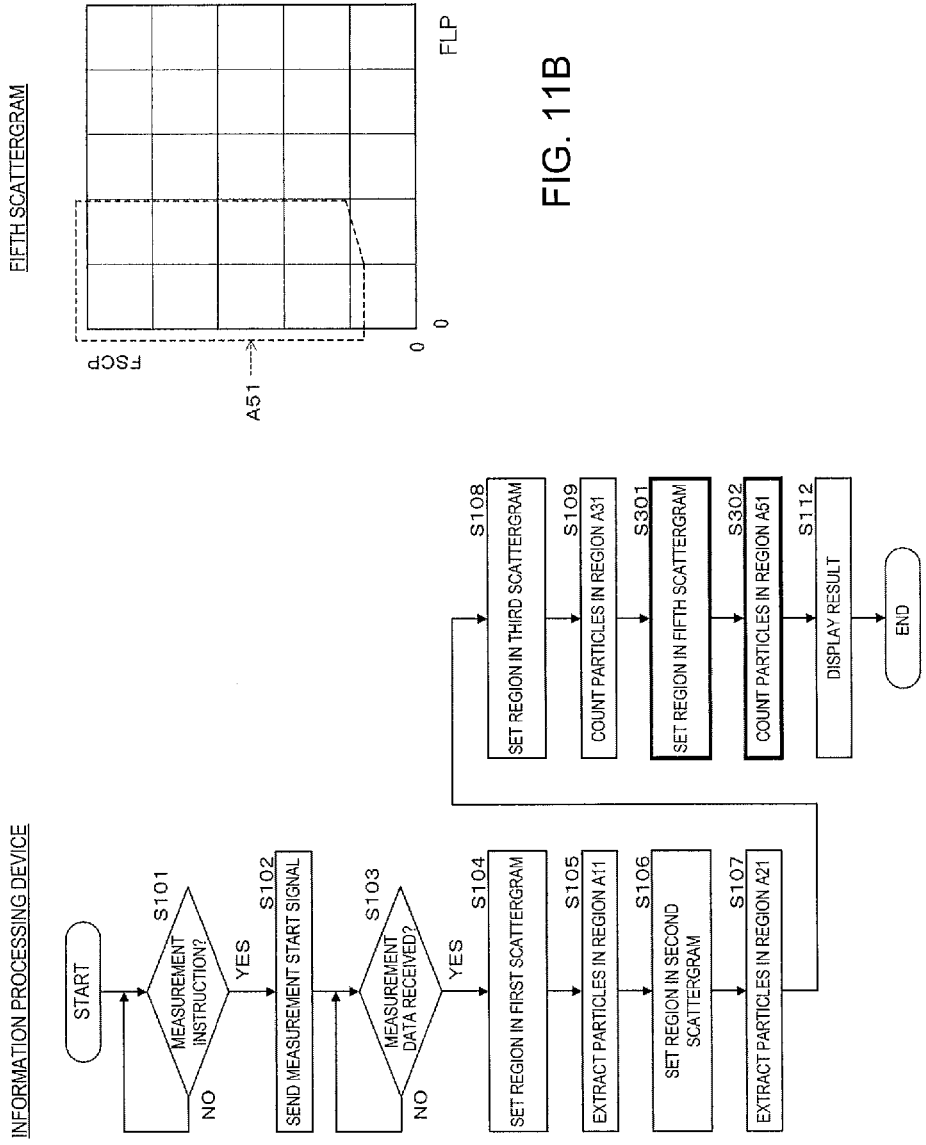

SAMPLE ANALYZING METHOD AND SAMPLE ANALYZER

RELATED APPLICATIONS

This application claims priority under 35 U.S.C. §119 to Japanese Patent Application No. 2013-178939 filed on Aug. 30, 2013, the entire content of which is hereby incorporated by reference.

FIELD OF THE INVENTION

The present invention relates to a sample analyzing method and sample analyzer for analyzing samples.

BACKGROUND OF THE INVENTION

There is known conventional art for detecting particles in urine samples using a flow cytometer. For example, Japanese Laid Open Patent JPH11-23446 discloses art for classifying several types of particles by detecting forward scattered light and fluorescent light from particles in a sample using a flow cytometer, and plotting the particles contained in the urine sample according to the intensity of the received light on a two-dimensional distribution diagram.

The prior art points out that since many types of particles are contained in urine samples, problems arise due to the mutual overlap of the distribution regions, particularly of erythrocytes and crystals. Considering these problems, the reliability and precision counting of erythrocytes was evaluated by the degree of overlap of the distributions of erythrocytes and crystals.

Since the number of erythrocytes in urine is extremely important information in the diagnosis of renal and urinary tract diseases, techniques are desirable for accurately counting erythrocytes even in urine samples containing a large numbers of crystals. Also, erythrocytes and crystals may be contained in body fluids other than blood or urine, especially in joint fluid. There is also a demand to improve an accuracy of classification of them in body fluids.

SUMMARY OF THE INVENTION

The scope of the present invention is defined solely by the appended claims, and is not affected to any degree by the statements within this summary.

A first aspect of the present invention is a sample analyzing method comprising: flowing a measurement specimen prepared by mixing a sample and reagent through a flow cell; irradiating particles in the measurement specimen flowing through the flow cell with linearly polarized light and thereby producing scattered light; detecting a change of polarization condition of the scattered light produced by the particles; and discriminating erythrocytes from crystals in the measurement specimen based on the change of polarization condition.

A second aspect of the present invention is a sample analyzing method comprising: flowing a measurement specimen prepared by mixing a sample and reagent through a flow cell; irradiating particles in the measurement specimen flowing through the flow cell with linearly polarized light and thereby producing scattered light; detecting a change of polarization condition of the scattered light produced by the particles; and discriminating crystals from other particles in the measurement specimen based on the change of polarization condition.

A third aspect of the present invention is a sample analyzer comprising: a preparing section that prepares a measurement specimen by mixing a sample and reagent; a flow cell through that flows the measurement specimen prepared by the preparing section; an optical detecting section that irradiates linearly polarized light on particles in the measurement specimen flowing through the flow cell to produce scattered light, and detect a change of polarization condition of the scattered light produced by each of the particles; and a computer programmed to discriminate erythrocytes from crystals based on the change of the polarization condition.

BRIEF DESCRIPTION OF THE DRAWINGS

FIG. 3 schematically shows the structure of the optical detecting device of the embodiment;

FIG. 4A illustrates a peak level; FIG. 4B illustrates a width; and FIG. 4C illustrates an area;

FIG. 7A shows the first scattergram of the embodiment;
FIG. 7B shows the second scattergram of the embodiment;
FIG. 7C shows the third scattergram of the embodiment;
FIG. 7D shows the fourth scattergram of the embodiment;
FIG. 8A shows the visual count results obtained by microscope, and results obtained by the embodiment;

FIG. 8B shows the third scattergram of an actual urine sample;

FIG. 8C shows the fourth scattergram of the actual urine sample;

FIG. 9A shows the visual count results obtained by microscope, and results obtained by the embodiment;

FIG. 9B shows the third scattergram of an actual urine sample;

FIG. 9C shows the fourth scattergram of the actual urine sample;

FIG. 11A shows a flowchart of modification;
FIG. 11B shows a fifth scattergram of modification.

DETAILED DESCRIPTION OF THE PREFERRED EMBODIMENTS

The embodiment is a urine sample analyzer for analyzing urine samples which contain particles such as blood cells, bacteria, casts, and epithelial cells. The urine samples to be measured include eliminated urine from a living body, secreted urine, primitive urine, urine of the urinary tract, urine in the bladder, and urine in the urethra. The urine analyzer flows the measurement specimen prepared by mixing urine sample and reagent through the flow cell. The urine analyzer irradiates linearly polarized light to the measurement specimen flowing through the flow cell, and detects the light produced by the irradiation of the particles in the measurement specimen. The urine analyzer obtains parameters reflecting the change of the polarization condition of the detected light, and classifies and counts erythrocytes and other particles such as crystals in the measurement specimen based on the parameter.

Erythrocytes and non-erythrocyte particles such as crystals respectively have their own characteristic components which have different polarization characteristics. When non-erythrocyte particles are irradiated with light, the polarization direction of the light thereby produced changes from the polarization direction of the light prior to irradiation of the particle according to the optical rotational power of the components contained in the particle. Especially crystals tend to change the polarization condition. However, when an erythrocyte is irradiated with light, the polarization direction of the light thereby produced is virtually unchanged from the polarization direction of the light prior to irradiation of the particle.

The present analyzer utilizes the characteristic differences. The analyzer obtains parameters reflecting the change of the polarization condition caused by each particle from the light produced by irradiating the particle. Then the analyzer classifies the particles as erythrocytes and non-erythrocyte particles such as crystals based on the difference in the parameters. Erythrocytes contained in the measurement specimen can be counted with excellent accuracy, and this may yield information useful for the diagnosis of renal and urinary disease as well as hemorrhagic disease.

This embodiment is described below with reference to the drawings.

Figure 1:
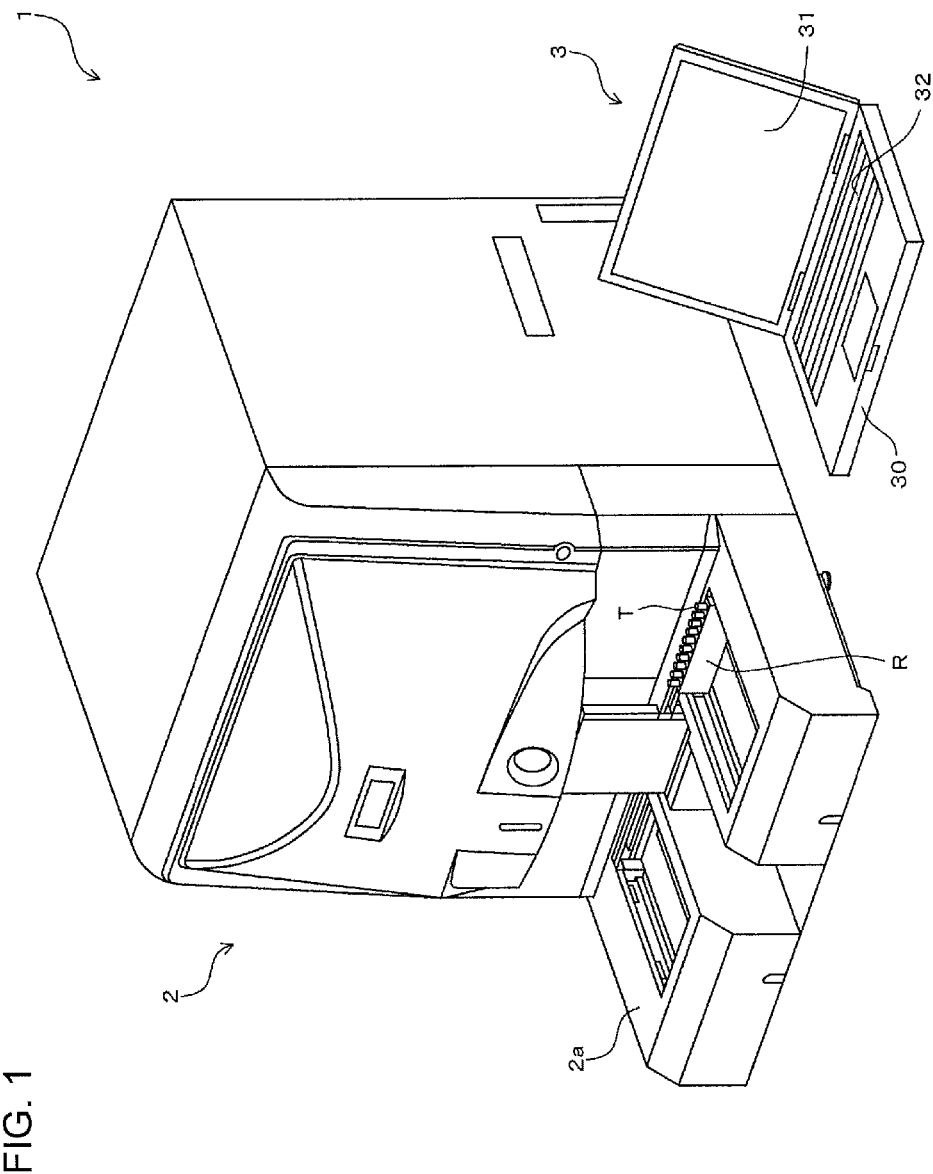
FIG. 1 shows an external view of a structure of the embodiment of the urine sample analyzer.

FIG. 1 shows the exterior structure of a urine sample analyzer 1.

The urine sample analyzer 1 has a measuring device 2 for optically measuring particles contained in the urine sample via flow cytometer, and an information processing device 3 for processing the measurement data output from the measuring device 2. A transporting unit 2a is provided in front of the measuring device 2, and the rack R holding a plurality of containers T containing urine samples is moved by the transporting unit 2a. The information processing device 3 is provided with a main body 30, display 31 for displaying analysis results and the like, and an input unit 32 for receiving instructions from the operator.

Figure 2:
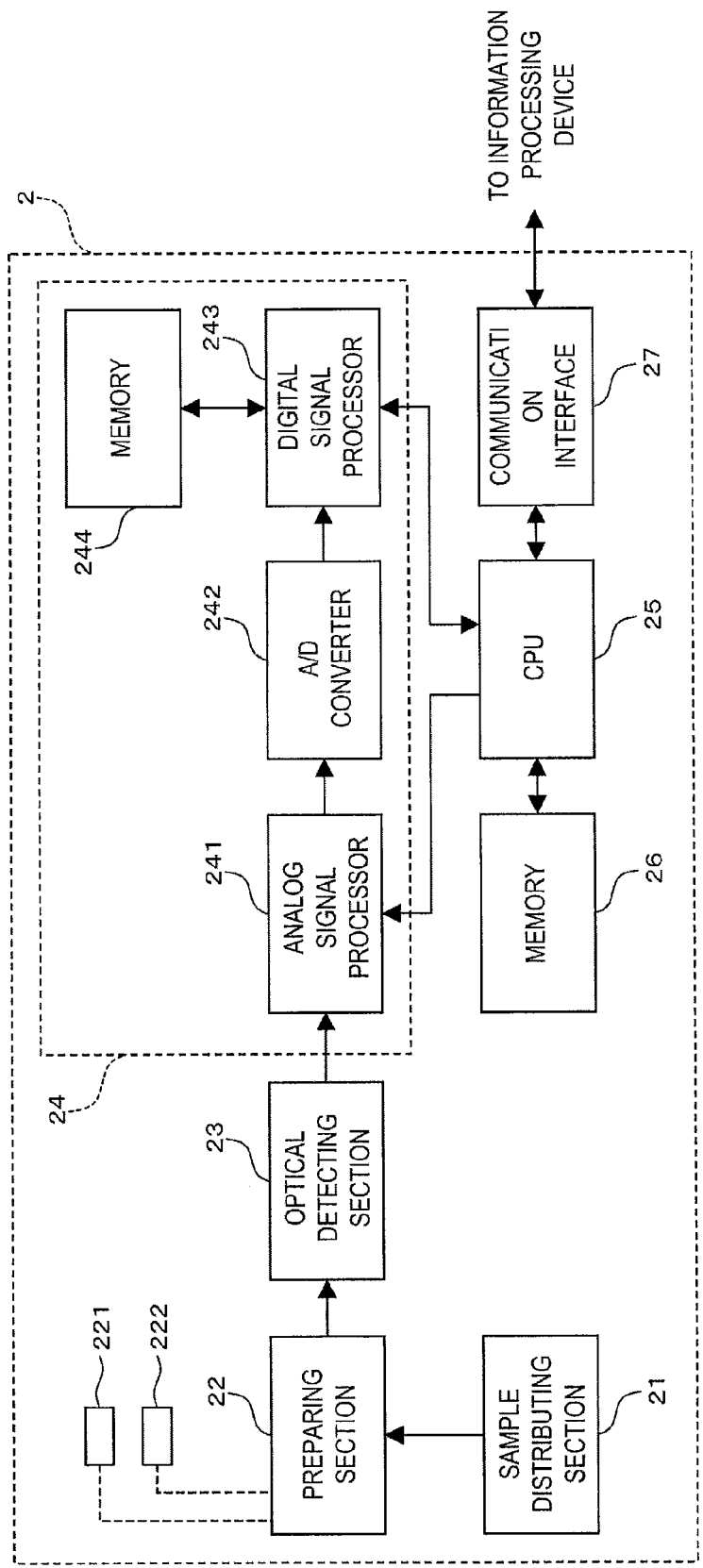
FIG. 2 shows the structure of the measuring device of the embodiment.

FIG. 2 shows the structure of the measuring device 2.

The measuring device 2 includes a sample distributing section 21, preparing section 22, optical detecting section 23, signal processing section 24, CPU 25, memory 26, and communication interface 27. The signal processing section 24 has an analog signal processor 241, A/D converter 242, digital signal processor 243, and memory 244.

The sample distributing section 21 aspirates a predetermined amount of urine sample from the container T transported by the transporting unit 2a, and supplies the aspirated sample to the preparing section 22. The preparing section 22 has a mixing chambers and a pump (not shown in the drawings). Containers 221 and 222 are connected through a tube to the preparing section 22. The container 221 contains reagent that includes stain for staining cell membrane and proteins, and container 222 contains diluting liquid. The sample supplied from the sample distributing section 21 into the mixing chamber is mixed with diluting liquid and reagent from the containers 221 and 222 to prepare the measurement specimen. The measurement specimen prepared in the mixing chamber is supplied together with sheath fluid to a flow cell 205 (refer to FIG. 3) of the optical detecting section 23.

FIG. 3 is a schematic view showing the structure of the optical detecting section 23.

The optical detection section 23 includes a light source 201, collimator lens 202, cylindrical lens 203, condenser lens 204, flow cell 205, collecting lens 206, beam stopper 207, pinhole 208, FSC detector 209, collecting lens 210, dichroic mirror 211, half mirror 212, SSC detector 213, polarization filter 214, PSSC detector 215, spectral filter 216, and SFL detector 217.

The light source 201 emits laser light having an approximate wavelength of 488 nm in the X-axis positive direction. The light source 201 is preferably a semiconductor laser light source. The laser light emitted from the light source 201 is linearly polarized light. The light source 201 is arranged within the measuring device 2 so that the polarization direction of the linearly polarized light is parallel to the direct (Z-axis direction) of the flowing measurement specimen at the laser light irradiation position on the flow cell 205. That is, the polarization direction of the light emitted from the light source 201 is perpendicular to the incidence surface when the incidence surface is perpendicular to the Z-axis direction.

The laser light from the light source 201 is converted to parallel rays by the collimator lens 202. The laser light that passes through the collimator lens 202 is converged only in the Y-axis direction by the cylindrical lens 203. The laser light that passes through the cylindrical lens 203 is collected in the Y-axis direction and Z-axis direction by the condenser lens 204. Hence, the laser light emitted from the light source 201 irradiates a beam narrow along the Y-axis direction on the measurement specimen flowing in the Z-axis direction within the flow cell 205. When the laser light irradiates particles in the measurement specimen, forward scattered light is produced in the forward direction (X-axis positive direction) of the flow cell 205, and side scattered light and side fluorescent light are produced in a lateral direction (Y-axis positive direction) of the flow cell 205.

The forward scattered light is collected at the position of the pinhole 208 by the collecting lens 206 arranged on the X-axis positive direction side of the flow cell 205. Among the light emitted from the light source 201, the laser light that passes through the flow cell 205 without illuminating particles in the measurement specimen is collected by the collecting lens 206, and then is blocked by the beam stopper 207 so as to not impinge the detector 209. The forward scattered light that passes through the pinhole 208 is detected by the FSC detector 209. The detector 209 outputs a forward scattered light signal (FSC) based on the detected forward scattered light.

The side scattered light is converged by the collecting lens 210 arranged on the Y-axis positive direction side of the flow cell 205. The side scattered light that passes through the collecting lens 210 is reflected by the dichroic mirror 211. The side scattered light reflected by the dichroic mirror 211 is split by the non-polarizing type half mirror 212. A part of the side scattered light that passes through the half mirror 212 is detected by the SSC detector 213. The SSC detector 213 outputs a side scattered light signal (SSC) based on the detected side scattered light. Another part of the side scattered light reflected by the half mirror 212 impinges the polarization filter 214.

When polarized laser light is irradiated on particles in the measurement specimen, the polarization direction of the side scattered light changes from the polarization direction of the laser light prior to irradiation of the particles according to the optical rotating power of the component contained in the particle. In the present embodiment, the polarization direction of the laser light irradiating the particles in the measurement specimen is parallel to the flow direction (Z-axis direction) of the measurement specimen flowing through the flow cell 205 (hereinafter, this polarization condition is referred to as the "initial polarization condition"). When the laser light is irradiated to the measurement specimen, the polarization direction of the laser light rotates to a polarization direction that differs from the initial polarization condition. As the polarization of the laser light is partially scrambled by irradiation on particles, the side scattered light produced in the Y-axis positive direction includes rays of various polarization conditions.

Among the rays of the side scattered light produced from the particles, the percentage of rays polarized perpendicular to the initial polarization direction, that is, degree of polarization scrambling is determined according to the component containing the particles. Erythrocytes and crystals have respectively components in different polarization characteristics, so erythrocytes and crystals can be classified based on the change of the polarization condition of the side scattered light, as will be described later.

The polarization filter 214 is configured to block the polarized light parallel to the Z-axis direction, and transmit the polarized light parallel to the X-axis direction. The side scattered light that has passed through the polarization filter 214 is referred to as "polarization scrambling side scattered light" or "PSSC light" hereinafter. The polarization scrambling side scattered light is detected by the PSSC detector 215. The PSSC detector 215 outputs a polarization scrambling side scattered light signal (PSSC) based on the detected polarization scrambling side scattered light.

As previously mentioned, the polarization direction of the side scattered light changes from the initial polarization condition according to the optical rotating power possessed by the particles in the measurement specimen. Therefore, the amount of polarization scrambling side scattered light that reaches the PSSC detector 215 also differs for each type of particle irradiated by the laser light, and the magnitude of the polarization scrambling side scattered light signal (PSSC) also differs for each type of particle irradiated by the laser light.

The forward scattered light emitted from the flow cell 205 and the side scattered light passed through the half mirror 212 are directly received by the FSC detector 209 and SSC detector 213, respectively, and do not pass through a polarization filter. Therefore, the FSC detector 209 detects the forward scattered light including rays of nonuniform polarization directions. The forward scattered light, similar to the side scattered light, has a polarization direction that changes from the initial polarization direction according to the optical rotating power of the particles in the measurement specimen.

Similar to the side scattered light, the side fluorescent light is converged by the collecting lens 210. The side fluorescent light that has passed through the collecting lens 210 subsequently passes through the dichroic mirror 211 and spectral filter 216, and is then detected by the SFL detector 217. The SFL detector 217 outputs a side fluorescent light signal (SFL) based on the detected side fluorescent light. Fluorescent light may be detected in other angle. For example, the fluorescent light can be detected in forward angle with respect to the irradiating light.

Returning now to FIG. 2, the optical detecting section 23 outputs the forward scattered light signals (FSC), side scattered light signals (SSC), polarization scrambling light signals (PSSC), and side fluorescent light signals (SFL) to the analog signal processor 241. The analog signal processor 241 amplifies, via an amplifier, the electrical signals from each detectors of the optical detecting section 23, and outputs the amplified electrical signals to the A/D converter 242.

The A/D converter 242 converts the electrical signals received from the analog signal processor 241 to digital signals, and outputs the digital signals to the digital signal processor 243. The digital signal processor 243 performs signal processing of the digital signals received from the A/D converter 242. Signal waveforms are obtained which correspond to the forward scattered light side scattered light, polarization scrambled side scattered light, and side fluorescent light produced when the particles pass through the flow cell 205. That is, signal waveforms corresponding to each type of light are obtained for each particle (erythrocytes, leukocytes, epithelial cells, casts, bacteria and the like) contained in the measurement specimen. The obtained signal waveforms are stored in the memory 244.

The CPU 25 calculates a plurality of characteristics parameters (peak level, width, area) corresponding to the forward scattered light, side scattered light, polarization scrambling side scattered light, side fluorescent light based on the signal waveforms stored in the memory 244.

Figure 4A:
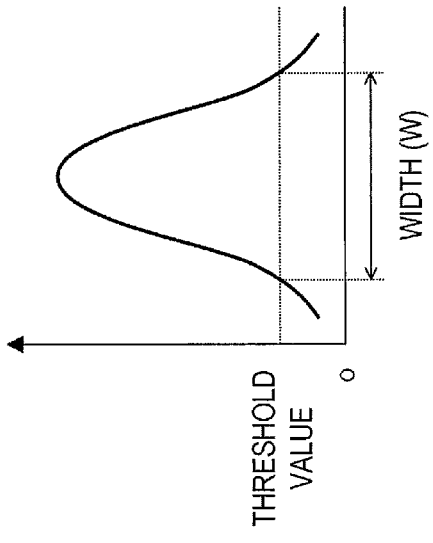
FIGS. 4A through 4C illustrate the characteristic parameters of the embodiment. Specifically.
Figure 4B:
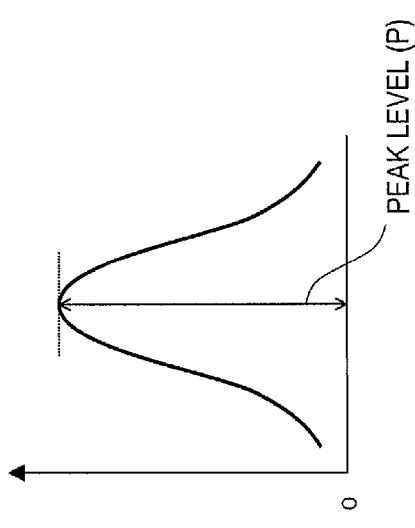
Figure 4C:
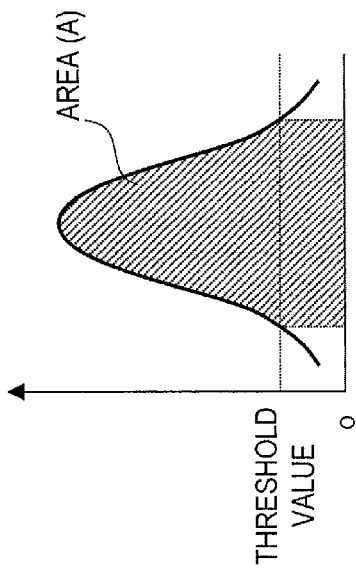

The peak level (P) is the maximum signal level of the pulse of the signal waveform, as shown in FIG. 4A. The width (W) is the width of the pulse of the signal waveform greater than a predetermined threshold value, as shown in FIG. 4B. The area (A) is the area of the pulse circumscribed by the signal waveform and the line segment extending downward from the origin of the intersection of the signal waveform and predetermined threshold values, as shown in FIG. 4C. The threshold values used in FIGS. 4B and 4C are suitably set according to the characteristics parameters to obtain appropriate characteristics parameters. The calculated characteristics parameters are stored in the memory 26.

The CPU 25 transmits the calculated characteristics parameters of each particle (hereinafter referred to as "measurement data") through the communication interface 27 to the information processing device 3. The CPU 25 receives the control signals from the information processing device 3 through the communication interface 27, and controls each part of the measuring device 2 according to these control signals.

Figure 5:
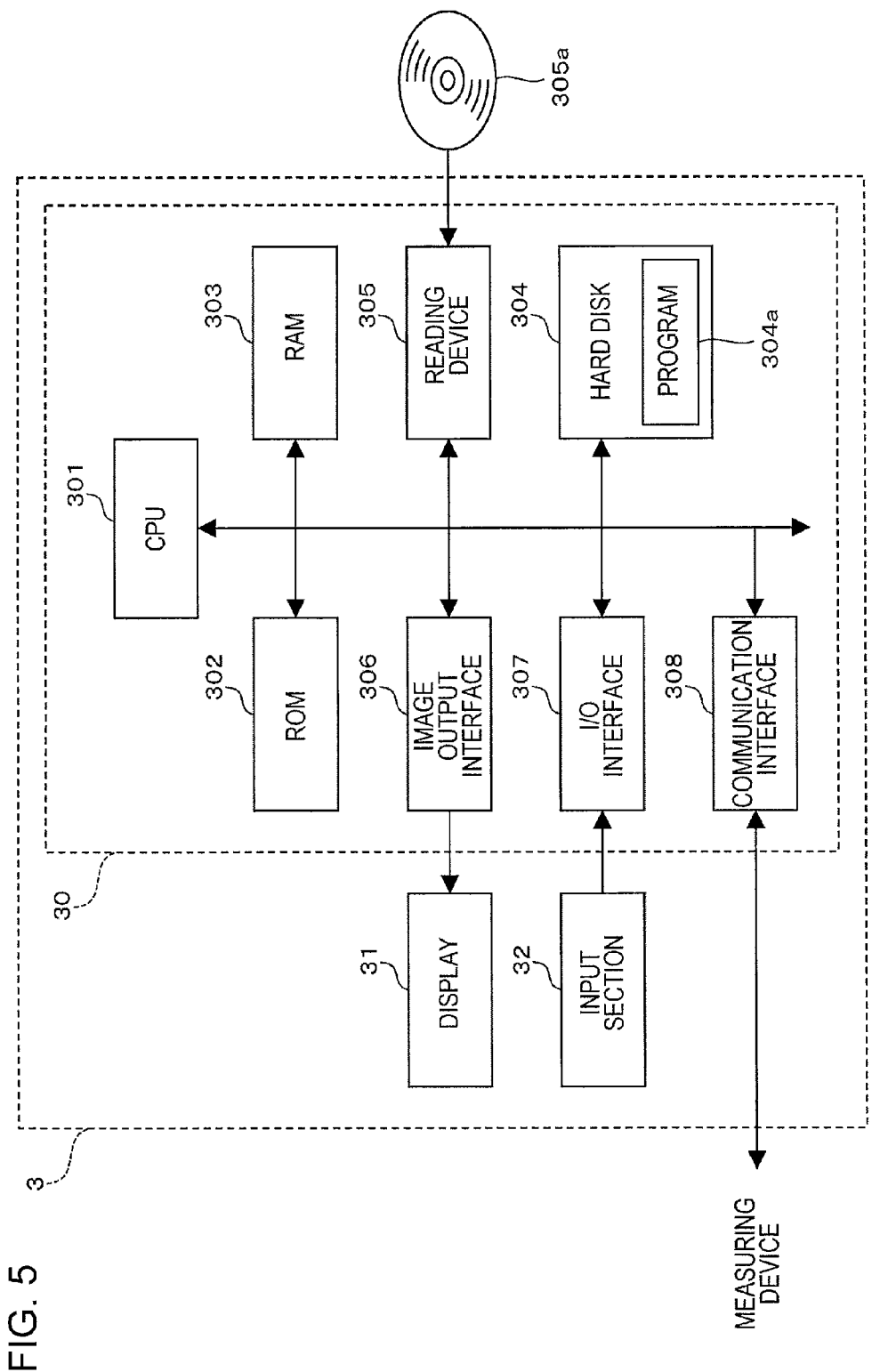
FIG. 5 shows the structure of the information processing device of the embodiment.

FIG. 5 shows the structure of the information processing device 3.

The information processing device 3 is configured by a personal computer that includes a main body 30, display 31, and input section 32. The main body 30 has a CPU 301 ROM 302, RAM 303, hard disk 304, reading device 305, image output interface 306, I/O interface 307, and communication interface 308.

The CPU 301 is capable of executing a computer program stored in the ROM 302 and a computer program loaded in the RAM 303. The RAM 303 is used when reading the computer program stored in the ROM 302 and recorded on the hard disk 304. The RAM 303 is also used as the work area of the CPU 301 when the CPU 301 executes the computer programs.

The hard disk 304 stores an operating system and computer programs, as well as the data used when executing the computer programs that are executed by the CPU 301. The hard disk 304 pre-stores a program 304a which performs the process shown in FIG. 6, and sequentially stores measurement data received from the measuring device 2. The reader 305 is a CD drive or DVD drive capable of reading computer programs and data recorded on a recording medium 305a. Note that when the program 304a is recorded on the recording medium 305a, the program 304a may be read from the recording medium 305a by the reading device 305 and stored on the hard disk 304.

The image output interface 306 outputs image signals corresponding to the image data to the display 31, and the display 31 displays the image based on the image signals. When the operator inputs instructions via the input section 32, the I/O interface 307 receives the input signals. The communication interface 308 is connected to the measuring device 2, and the CPU 301 sends and receives instruction signals and data to/from the measuring device 2 through the communication interface 308.

Figure 6:
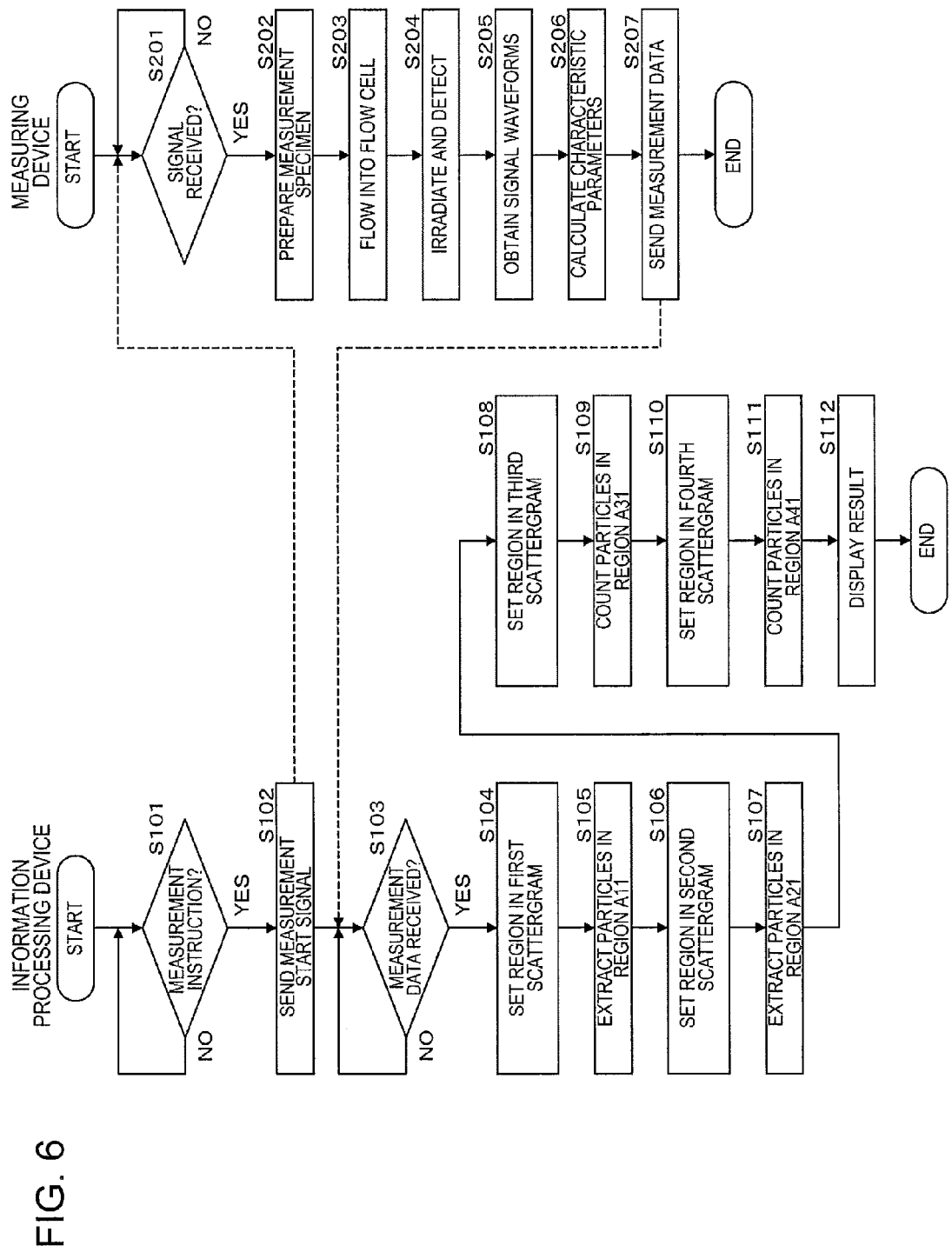
FIG. 6 is a flow chart showing the processes of the measuring device and information processing device of the embodiment.

FIG. 6 is a flow chart showing the processes performed by the measuring device 2 and the information processing device 3.

When the CPU 301 of the information processing device 3 receives a measurement instruction from the operator via the input section 32 (S101: YES), the CPU 301 transmits a measurement start signal to the measuring device 2 (S102). When the CPU 25 of the measuring device 2, on the other hand, receives a measurement start signal from the information processing device 3 (S201: YES), the CPU 25 controls the preparing section 22 to prepare a measurement specimen (S202). The CPU 25 controls the preparing section 22 to supply the prepared measurement specimen to the flow cell 205 so that the measurement specimen flows in the flow cell 205 (S203). Then, laser light emitted from the light source 201 irradiates the measurement specimen flowing through the flow cell 205, and forward scattered light, side scattered light, polarization scrambling side scattered light, and side fluorescent light of each particle contained in the measurement specimen are respectively detected by the FSC detector 209, SSC detector 213, PSSC detector 215, and SFL detector 217 (S204).

The CPU 25 then obtains the signal waveforms corresponding to each type of detected light (S205), and calculates the several characteristics parameters based on the obtained signal waveforms (S206). The CPU 25 then transmits the several calculates characteristics parameters (measurement data) of each particle to the information processing device 3 (S207).

On the other hand, when the CPU 301 of the information processing device 3 receives the measurement data (S103: YES), the CPU 301 sets the region A11 in the first scattergram which includes an axis of the width of the forward scattered light signals and an axis of the peak level of the forward scattered light signals (FSCP) (S104). As shown in FIG. 7A, the CPU 301 plots each particle contained in the measurement data in the first scattergram according to the magnitude of FSCW and the magnitude of FSCP.

In FIG. 7A, the region A11 corresponds to the erythrocytes and crystals contained in the measurement specimen. The other region corresponds to casts, bacteria, and debris. The CPU 301 extracts the particles included in region A11 in the first scattergram (S105).

In the above description particles are plotted in the first scattergram and the particles contained in region A11 of the first scattergram are extracted. However, the region A11 of the first scattergram need not necessarily be defined as a diagram or graph. Extraction of particles contained in region A11 also may be accomplished by data processing to extract only those particles related to a specific numerical range via sorting or filtering. Similarly, the regions A21, A22, A31, A32, A41, A51 of the second through fifth scattergrams which will be described later need not necessarily be defined as a diagram or graph since the total number of particles contained in regions A31 and A41 may also be obtained by data processing such as sorting or filtering.

The CPU 301 then sets the regions A21 and A22 in the second scattergram which includes an axis of the peak level of the polarization scrambling side scattered light signal (PSSCP) and an axis of the peak level of the forward scattered light signals (FSCP) (S106). The CPU 301 plots the particles in region A11 extracted in S105 in the second scattergram according to the magnitude of PSSCP and the magnitude of FSCP, as shown in FIG. 7B.

The vertical axis PSSCA represents an amount of light polarized perpendicularly to the initial polarization direction which is proportional to the degree of polarization scrambling triggered by the particle. Crystals which largely contains the component to scramble polarization, compared to the erythrocytes, are distributed in the region of high PSSCP. Therefore the regions A21 and A22 respectively correspond to the erythrocytes and crystals.

Neither erythrocytes nor crystals have a nucleus and both are similar in size. Therefore, sometimes accurate classification of those may have been difficult without using polarization scrambling side scattered light. In the present embodiment, erythrocytes and crystals are classified using polarization scrambling side scattered light. Polarization scrambling is not likely to be triggered by an erythrocyte compared to a crystal. Thus, distinguishing erythrocytes and crystals are accomplished by setting the regions A21 and A22. This makes it possible to accurately discriminate erythrocytes and crystals compared to conventional arts without using polarization scrambling.

Referring back to FIG. 6, the CPU 301 extracts the particles contained in region A21 of the second scattergram (S107).

The CPU 301 then sets the regions A31 and A32 in the third scattergram which includes an axis of the peak level of the side fluorescent light signals (FLP) and an axis of the peak level of the forward scattered light signals (FSCP) (S108). The CPU 301 plots the particles extracted in S107 in the third scattergram according to the magnitude of FLP and the magnitude of FSCP as shown in FIG. 7C.

The horizontal axis FLHP in FIG. 7C represents the degree of staining of the most intensely stained part of the particle. Erythrocytes are distributed at the high FLP region than other components such as debris and residual crystals and the like because the cell membrane of erythrocyte is deeply stained by the stain. Other components are distributed at the low FLP region. The vertical axis FSCP represents the size of the particles. The vertical range (FSCP) of A31 is set according to the known size of erythrocytes. Thus the regions A31 and A32 in FIG. 7C respectively correspond to erythrocytes and other components. The region A32 may contain crystals in addition to debris which could not be removed in S106 and S107.

The CPU 301 counts the particles contained in region A31 of the third scattergram as the number of erythrocytes (S109). The number of erythrocytes contained in the measurement specimen is thus obtained.

The CPU 301 then sets the region A41 in the fourth scattergram which includes an axis of the peak level of the side fluorescent light signals (FLP) and an axis of the peak level of the forward scattered light signals (FSCP) (S110). The CPU 301 excludes the erythrocytes counted in S109 from the particles extracted in S105 and plots the remaining particles in the fourth scattergram as shown in FIG. 7D.

Substantially all of the particles plotted in the fourth scattergram are crystals. Plots in the fourth scattergram include very few erythrocytes or do not include erythrocytes. The crystals contained in the measurement specimen therefore can be accurately extracted from region A41.

The CPU 301 counts the particles contained in region A41 of the third scattergram as the number of the crystals (S111). The number of crystals is thereby obtained.

The CPU 301 then shows the number of erythrocytes obtained in S109, and the number of crystals obtained in S111 on the display 31 (S112). The processes of the measuring device 2 and the information processing device 3 are thus completed.

The count results of an actual urine sample visually obtained via microscope and the count results of the urine sample obtained by the present embodiment were compared.

FIG. 8A shows the count results of a specific urine sample visually obtained via microscope and the count results of the urine sample obtained by the present embodiment. The urine sample contained 2288.0 cells/pt of erythrocytes, and 0.0 crystals/µL according to the visual count results. FIG. 8B and FIG. 8C respectively show the third and fourth scattergrams of the embodiment for the specific urine sample.

Erythrocytes are abundant in urine collected from patient of renal and urinary tract ailments and hemorrhagic disease. Generally, if there are more than 20 erythrocytes in a 1 µL urine sample, the subject from whom the urine sample was collected has a high possibility of renal or urinary tract disease or hemorrhagic disease.

According to the visual count results of FIG. 8A, there are more than 20 erythrocytes contained in the 1 µL urine sample. According to the results of the present embodiment shown in FIG. 8A, the erythrocytes contained in 1 µL urine sample is also more than 20, similar to the visual results. Referring to FIGS. 8B and 8C, a high number of particles are contained in the region A31 and few particles are contained in region A41. It is understood that the urine sample contains many erythrocytes and few crystals. According to the present embodiment, the operator can determine there is a high possibility the patient has renal or urinary tract disease or hemorrhagic disease based on the many erythrocytes in the urine sample collected from the patient, similar to the visual results.

FIG. 9A shows the count results obtained visually via microscope and the count results of the present embodiment concerning another urine sample which is different from the urine sample of FIG. 8A through 8C. The urine sample in this case contained 0.0 cells/µL of erythrocytes, and 160.0 crystals/µL according to the visual count results. FIGS. 9B and 9C shows the third and fourth scattergrams of the embodiment for the specific urine sample.

According to the visual count results of FIG. 9A, there are fewer than 20 erythrocytes contained in the 1 µL urine sample. According to the results of the present embodiment shown in FIG. 9A, the number of erythrocytes contained in 1 µL urine sample is also fewer than 20, similar to the visual results. Referring to FIG. 9B the erythrocytes contained in the urine sample are understood to be few in number because the number of particles included in region A31 is low. Referring to FIG. 9C, the crystals are understood to be classified properly since a certain number of particles are contained in region A41. According to the present embodiment, the operator can determine there is a low possibility the patient has renal or urinary tract disease or hemorrhagic disease based on the few erythrocytes in the urine sample collected from the patient, similar to the visual results.

Thus erythrocytes can be accurately counted in the present embodiment because crystals can be distinguished from erythrocytes in the urine sample as described above. Since crystals are contained in urine of healthy person, it is difficult to specify the disease based only on the number of crystals. However, when crystals and erythrocytes are abundant in urine, specific disease is suspected. Therefore the number of crystals has a clinical meaning.

According to the present embodiment, particles are plotted in the second scattergram having axes of PSSCP and FSCP, and then the particles in region A21 which have low PSSCP are plotted in the third scattergram having axes of FLP and FSCP. In the third scattergram, highly stained particles are counted as erythrocytes. The accuracy of the erythrocyte count is therefore improved because the crystals and other particles are removed from the region for counting the erythrocyte based on PSSCP.

The present embodiment also provides information useful in the diagnosis of renal and urinary tract disease and hemorrhagic disease by accurately counting erythrocytes. More specifically, the number of erythrocytes can be accurately obtained and the obtained number can be displayed by counting the number of particles in region A31 of the third scattergram. The operator therefore can determine the patient has a high possibility of renal or urinary tract disease or hemorrhagic disease based on an abundance of erythrocytes.

Figure 10:
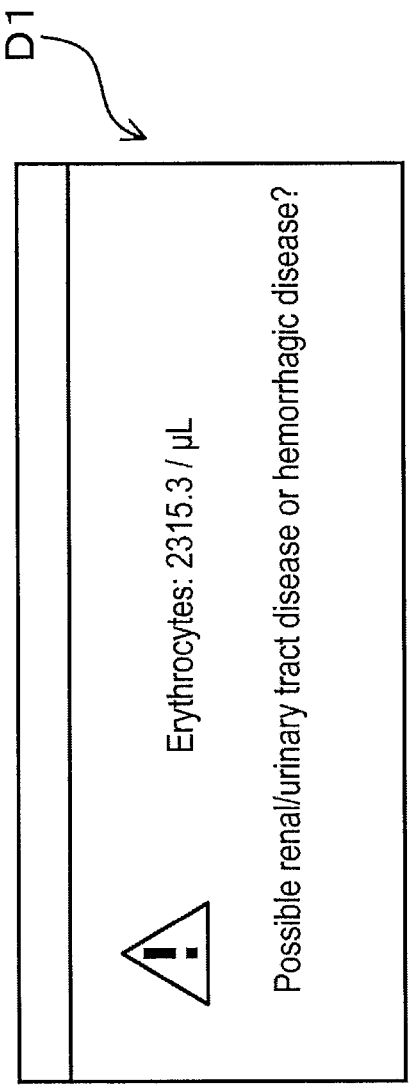
FIG. 10 shows a screen shown on the display section of a modification.

The screen D1 of FIG. 10 may be shown on the display 31 of the information processing device 3 in S112 of FIG. 6, when the number of erythrocytes is higher than a threshold number (e.g. 20). Screen D1 shows the basis for determining a high possibility of renal or urinary tract disease or hemorrhagic disease, that is the number of erythrocytes, and suggests the possibility of morbidity. In S112 of FIG. 6, the second through fourth scattergrams also may be displayed together.

According to the present embodiment, the polarization direction of the laser light emitted from the light source 201 is parallel to the flow direction (Z-axis direction) of the measurement specimen flowing through the flow cell 205. Therefore, since fluorescent light is produced in the approximate Y-axis direction when the laser light is irradiated in the X-axis positive direction relative to the particles flowing through the flow cell 205, the side scattered light and fluorescent light can be received in approximately the same direction (Y-axis positive direction). The structure of the optical detecting section 23 therefore can be simplified. When the optical detecting section 23 is configured as described above, side fluorescent light is more efficiently detected by the SFL detector 217 arranged on the Y-axis positive side of the flow cell 205.

According to the present embodiment, the PSSC detector 215 can efficiently detect the polarization scrambling side scattered light because the polarization filter 214 blocks the side scattered light that has the same polarization direction as the laser light irradiating the measurement specimen.

Although described by way of the above embodiments, the present invention is not limited to these embodiments and may be variously modified.

Although the light source 201 emits linearly polarized light in the above embodiment, the present invention is not limited to this configuration inasmuch as a light source module may be used which combines a generally used light source for emitting non-polarized light and a polarization filter configured to transmit only rays of single polarization direction.

Although the light source 201 is arranged within the measuring device 2 so that the polarization direction of the linearly polarized light is parallel to the direction (Z-axis direction) of the flowing measurement specimen at the laser light irradiation position on the flow cell 205. However, the polarization direction of the laser light emitted from the light source 201 need not necessarily match the flow direction of the measurement specimen, and may be inclined relative to the direction of the flow of the measurement specimen. In this case, the travel direction of the fluorescent light moving from the particle will be distanced from the Y-axis direction compared to the above embodiment. Since the fluorescent light is efficiently detected by the SFL detector 217, the polarization direction of the laser light emitted from the light source 201 preferably matches the flow direction of the measurement specimen as in the above embodiment.

Although the peak level of the polarization scrambling side scattered light signals (PSSCP) is used as one of the axes in the second scattergram in the above embodiment, other characteristics parameters can be utilized as far as that reflect the degree of polarization scrambling by the particles. For example, the area of the polarization scrambling side scattered light signals (PSSCA) also may be used. In this case, whether the PSSCA or PSSCP is used as the characteristics parameter of the horizontal axis can be appropriately set according to the size of the beam spot of the laser light irradiating the measurement specimen, the speed of the measurement specimen flowing through the flow cell 205, and the amplification of the analog signal processing unit 241.

The characteristics parameter that reflects the degree of polarization scrambling (the vertical axis of the second scattergram) may be obtained from the forward scattered light. As described above, the forward scattered light impinging the FSC detector 209 includes several rays of polarization direction. Therefore, if a half mirror is arranged on the X-axis negative direction side of the FSC detector 209 and the forward scattered light split by the half mirror then passes through a polarization filter, the optical component (polarization scrambling forward scattered light) in a polarization direction different from the initial polarization direction can be received among the forward scattered light from the particles.

Instead of the second scattergram, a histogram may be used in which the peak level of the polarization scrambling side scattered light signals (PSSCP) is scaled as the horizontal axis, and the number of particles is plotted on the vertical axis. In this case, particles in the range of low PSSCP are extracted from the histogram as erythrocytes, similar to region A21 of the second scattergram.

Although the peak level of the side fluorescent light signals (FLP) is used in the horizontal axis in the third and fourth scattergrams in the above embodiment, other characteristics parameters may be utilized as far as that reflects the degree of stain. For example, the horizontal axis may be the area of the side fluorescent light signals (FLA). In this case, whether the FLHA or FLHP is used as the characteristics parameter of the horizontal axis can be appropriately set according to the size of the beam spot of the laser light irradiating the measurement specimen, the speed of the measurement specimen flowing through the flow cell 205, and the amplification of the analog signal processing unit 241.

Although the peak level of the forward scattered light signals (FSCP) is used in the vertical axis of the third and fourth scattergrams in the above embodiment, other characteristics parameters may be utilized as far as that reflects the size of the particles. For example, the area of the forward scattered light signals (FSCA) also may be plotted on the vertical axis. Or by detecting an amount of loss of light by particle which is proportional to project area of the particle may be used as the parameter of size. Preferable characteristics parameter of the vertical axis can be appropriately selected according to the size of the beam spot of the laser light irradiating the measurement specimen, the speed of the measurement specimen flowing through the flow cell 205, and the amplification of the analog signal processing unit 241.

In the above embodiment, the number of crystals are counted by excluding erythrocytes from the particles extracted in S105, and plotting the remaining particles in the fourth scattergram. However, particles contained in region A22 may be directly counted as crystals. Or, by plotting the particles in the region A22 to the region A32, crystals may be counted as the number of plots in the A32.

Although the characteristics parameters reflecting the size of the particles are generated based on the forward scattered light signals detected by the optical detecting section 23 in the above embodiment, the characteristics parameters also may be generated based on the signals detected by an electrical resistance type sensor provided separately in the measuring device 2.

In the above embodiment, a light source 201 is provided in the measuring device 2 so that the polarization direction of the laser light emitted from the light source 201 is uniformed to parallel to the flow direction of the measurement specimen flowing through the flow cell 205. In an alternative, a ½ wavelength plate may be provided on the exit side of the light source 201 so as to adjust the polarization direction of the laser light emitted from the light source 201 to be parallel to the flow direction of the measurement specimen flowing through the flow cell 205.

Although the regions A11, A21, A22, A31, A32, and A41 are fixed regions determined beforehand in the above embodiment, the regions may be appropriately fine tuned based on the fixed region. The position and shape of the regions A11, A21, A11, A31, A32, and A41 are not necessarily limited to those shown in FIG. 7A through 7D, and may be appropriately adjusted to positions and shapes which allow more precise extraction of erythrocytes and crystals.

The structure of the optical system is not necessarily limited to the structure shown in FIG. 3, and may be configured to obtain characteristics parameters to distinguish erythrocytes and crystals based on the degree of optical rotational power. For example, the transmission polarization direction of the polarization filter 214 need not necessarily be parallel to the X-axis direction, and may be inclined from the X-axis direction in a range of the optical rotational power can be observed.

Discrimination and counting crystals may be performed by other sequence. FIG. 11A shows a flow chart showing the processing of the information processing device 3 according modification. In FIG. 11A, the steps S110, S111 are replaced with steps S301, S302. The process of S301, S302 are described below.

After completion of step S109, the CPU301 of the information processing device 3 sets the region A51 in the fifth scattergram (S301). The CPU 301 plots the particles in the area A22 to the fifth scattergram as shown in FIG. 11B. The axes of the fifth scattergram are same with those of the fourth scattergram. The region A51 is defined as same as the region A41. The CPU 301 counts the particles in the region A51 as the crystals.

Note that the present invention is not limited to the above described embodiments and may be variously modified insofar as such modification are within the scope of the claims.

What is claimed is:
1. A sample analyzing method comprising:
    flowing a measurement specimen prepared by mixing a sample and reagent through a flow cell;
    irradiating particles in the measurement specimen flowing through the flow cell with linearly polarized light and thereby producing scattered light;
    detecting the scattered light having a polarization direction that differs from that of the irradiating light, the polarization direction of the scattered light being changed by the particles;
    obtaining sizes of the particles based on other part of light produced by the irradiation;
    discriminating erythrocytes from crystals in the measurement specimen based on a difference of the change of polarization direction and a difference of the sizes; and
    sending results of the discriminated erythrocytes to be displayed on a processor controlled display device.

2. The sample analyzing method of claim 1, wherein the detection of the scattered light includes detecting at least a part of the scattered light produced by a polarization scrambling which a particle triggered.

3. The sample analyzing method of claim 1, wherein the irradiating light is polarized parallel to the flow direction of the measurement specimen; and
the detection of the scattered light includes detecting a part of the scattered light having a polarization direction perpendicular to that of the irradiating light.

4. The sample analyzing method of claim 1, further comprising
transmitting a part of the scattered light having a polarization direction different from that of the irradiating light to a detector via a polarization filter; and
blocking at least a part of the scattered light having a polarization direction same with that of the irradiating light via the polarization filter.

5. The sample analyzing method of claim 1, further comprising:
detecting fluorescent light produced by irradiating particles; and
wherein the erythrocytes are discriminated from the crystals based on the difference of the change of polarization direction and the fluorescent light.

6. The sample analyzing method of claim 1, further comprising:
extracting a group of particles including erythrocytes and crystals from the particles in the measurement specimen by a processor;
classifying the group into erythrocytes and crystals based on the difference of the changes of the polarization directions by the processor; and
counting the classified erythrocytes and crystals by the processor.

7. The sample analyzing method of claim 1, further comprising:
extracting a first group of particles including erythrocytes and crystals from the particles in the measurement specimen by a processor;
classifying the first group into second and third groups by the processor, wherein the particles in the second group possesses lower ability of changing the polarization directions compared to those of the third group; and
counting at least a part of the particles in the second group as erythrocytes by the processor.

8. The sample analyzing method of claim 7, further comprising
excluding the particles which are not stained well with a membrane staining dye from the second group by the processor, wherein the reagent contains the membrane staining dye; and
counting the remaining particles in the second group as erythrocytes by the processor.

9. The sample analyzing method of claim 7, further comprising
counting at least a part of the particles in the third group as crystals by the processor.

10. The sample analyzing method of claim 1, wherein the sample is urine or body fluid other than urine or blood.

11. The sample analyzing method of claim 1, further comprising
displaying a message suggesting a possibility of disease when the number of the discriminated erythrocytes is higher than a threshold.

12. A sample analyzing method comprising:
flowing a measurement specimen prepared by mixing a sample and reagent through a flow cell;
irradiating particles in the measurement specimen flowing through the flow cell with linearly polarized light and thereby producing scattered light;
detecting the scattered light having a polarization direction that differs from that of the irradiating light, the polarization direction of the scattered light being changed by the particles;
obtaining sizes of the particles based on other part of light produced by the irradiation;
discriminating crystals from other particles in the measurement specimen based on difference of the change of polarization direction and a difference of the sizes; and
sending results of the discriminated crystals to be displayed on a processor controlled display device.

13. A sample analyzer comprising:
a preparing section that prepares a measurement specimen by mixing a sample and reagent;
a flow cell that flows the measurement specimen prepared by the preparing section;
an optical detecting section that irradiates linearly polarized light on particles in the measurement specimen flowing through the flow cell to produce scattered light, and detect the scattered light having a polarization direction that differs from that of the irradiating light, the polarization direction of the scattered light being changed by the particles;
a computer programmed to obtain sizes of the particles based on other part of light produced by the irradiation, and discriminate erythrocytes from crystals based on a difference of the change of the polarization direction and a difference of the sizes; and
send results of the discriminated erythrocytes to be displayed on a processor controlled display device.

14. The sample analyzer of claim 13, wherein the optical detecting section detects at least a part of the scattered light produced by a polarization scrambling which the particle triggered.

15. The sample analyzer of claim 13, wherein the optical detecting section irradiates light polarized parallel to the flow direction of the measurement specimen, and detects scattered light polarized perpendicular to the polarization direction of the irradiating light.

16. The sample analyzer of claim 13, wherein the optical detecting section comprises:
a detector arranged to detect a part of the scattered light produced by particles; and
a polarization filter arranged in the light path between the detector and the flow cell to transmit a part of the scattered light having a polarization direction different from that of the irradiating light to the detector and to block at least a part of the scattered light having a polarization direction same with that of the irradiating light.

17. The sample analyzer of claim 13, wherein the computer is programmed to:
extract a first group of particles including erythrocytes and crystals from the particles in the measurement specimen;
classify the first group into second and third groups, wherein the particles in the second group possesses lower ability of changing the polarization directions compared to those of the third group; and
count at least a part of the particles in the second group as erythrocytes.

18. The sample analyzing method of claim 1, further comprising obtaining peak levels of waveforms of the scattered light produced from the particles, wherein the difference of the change of polarization direction is a difference of the peak levels.

19. The sample analyzing method of claim 18, wherein the scattered light is side scattered light, and the other part of light is forward scattered light, and the sizes of the particles are peak levels of signal waveforms of the forward scattered light.

20. A sample analyzing method comprising:
flowing a measurement specimen prepared by mixing a sample and reagent through a flow cell;
irradiating particles in the measurement specimen flowing through the flow cell with linearly polarized light and thereby producing side scattered light and forward scattered light;
detecting the side scattered light having a polarization direction that differs from that of the irradiating light, the polarization direction of the side scattered light being changed by the particles;
detecting the forward scattered light;
obtaining first peak levels of signal waveforms of the side scattered light;
obtaining second peak levels of signal waveforms of the forward scattered light;
discriminating erythrocytes from crystals in the measurement specimen based on a difference of the first peak levels and a difference of the second peak levels; and
send results of the discriminated erythrocytes to be displayed on a processor controlled display device.

21. A sample analyzer comprising:
preparing section that prepares a measurement specimen by mixing a sample and reagent:
a flow cell that flows the measurement specimen prepared by the preparing section:
an optical detecting section that irradiates linearly polarized light on particles in the measurement specimen flowing through the flow cell to produce side scattered forward scattered light, and detects the side scattered light having a polarization direction that differs from that of the irradiating tight, the polarization direction of the side scattered light being changed by the particles, and detects the forward scattered light; and
a computer programmed to:
obtain first peak levels of signal waveforms of the side scattered
obtain second peak levels of signal waveforms of the forward scattered light; and
discriminate erythrocytes from crystals in the measurement specimen based on a difference of the first peak levels and a difference of the second peak levels; and
send results of the discriminated erythrocytes to be displayed on a processor controlled display device.

\* \* \* \* \*